(12) United States Patent
Sahin

(10) Patent No.: US 10,231,691 B2
(45) Date of Patent: Mar. 19, 2019

(54) AUDIBLE ULTRASOUND PHYSICAL EXAMINATION DEVICE

(71) Applicant: Mustafa Behnan Sahin, Rapid City, SD (US)

(72) Inventor: Mustafa Behnan Sahin, Rapid City, SD (US)

( * ) Notice: Subject to any disclaimer, the term of this patent is extended or adjusted under 35 U.S.C. 154(b) by 432 days.

(21) Appl. No.: 15/260,498

(22) Filed: Sep. 9, 2016

(65) Prior Publication Data
US 2018/0070913 A1    Mar. 15, 2018

(51) Int. Cl.
*A61B 7/04* (2006.01)
*A61B 5/00* (2006.01)
*A61B 7/00* (2006.01)

(52) U.S. Cl.
CPC .............. *A61B 7/04* (2013.01); *A61B 5/7405* (2013.01); *A61B 7/00* (2013.01)

(58) Field of Classification Search
CPC ........................................................ A61B 7/04
See application file for complete search history.

(56) References Cited

U.S. PATENT DOCUMENTS

| | | | | |
|---|---|---|---|---|
| 4,413,629 | A | * | 11/1983 | Durley, III ........... A61B 5/0011 600/453 |
| 5,960,089 | A | * | 9/1999 | Bouricius ................ A61B 8/08 381/67 |
| 9,078,571 | B2 | | 7/2015 | Bridger et al. |
| 2009/0279708 | A1 | | 11/2009 | Habboushe |
| 2015/0327775 | A1 | | 11/2015 | Carter |

FOREIGN PATENT DOCUMENTS

| | | |
|---|---|---|
| CA | 02575075 | 11/2015 |
| CN | 20002017237 | 10/2001 |
| CN | 20092025013 | 4/2010 |
| CN | 2011210167 | 11/2011 |
| JP | 19990161506 | 11/2000 |
| WO | WO2008112693 | 9/2008 |

\* cited by examiner

Primary Examiner — Olisa Anwah

(57) ABSTRACT

An audible ultrasound physical examination device alters ultrasound to an audible range such that audible feedback can be used to enhance physical examination to detect anatomical abnormality and determine if more refined testing is warranted. The device includes a chestpiece and an ultrasound probe coupled to the chestpiece. The ultrasound probe projects an initial sound wave towards a first face of the chestpiece and into a human body such that a reflected wave is produced when the initial sound wave is reflected by matter with the human body. A sonic converter, coupled to the chestpiece, introduces an interference wave creating destructive interference to produce a resulting wave within an audible range. An earpiece is coupled to the chestpiece such that the resulting wave in the audible range is audible through the earpiece.

13 Claims, 6 Drawing Sheets

AUDIBLE ULTRASOUND PHYSICAL EXAMINATION DEVICE

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIE THE OFFICE ELECTRONIC FILING SYSTEM.

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

(2) Description of Related Art Including Information Disclosed Under 37 CFR 1.97 and 1.98

The disclosure and prior art relates to physical examination devices and more particularly pertains to a new physical examination device for projecting ultrasound and altering feedback to an audible range through heterodyne wave principles such that changes in audible feedback while probing can be used to identify potential health concerns and determine if more refined testing is warranted.

BRIEF SUMMARY OF THE INVENTION

An embodiment of the disclosure meets the needs presented above by generally comprising a chestpiece and an ultrasound probe coupled to the chestpiece. The ultrasound probe projects an initial sound wave towards a first face of the chestpiece and into a human body such that a reflected wave is produced when the initial sound wave is reflected by matter within the human body. A sonic converter, coupled to the chestpiece, introduces an interference wave creating destructive interference to produce a resulting wave within an audible range. An earpiece is coupled to the chestpiece such that the resulting wave in the audible range is audible through the earpiece.

There has thus been outlined, rather broadly, the more important features of the disclosure in order that the detailed description thereof that follows may be better understood, and in order that the present contribution to the art may be better appreciated.

There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
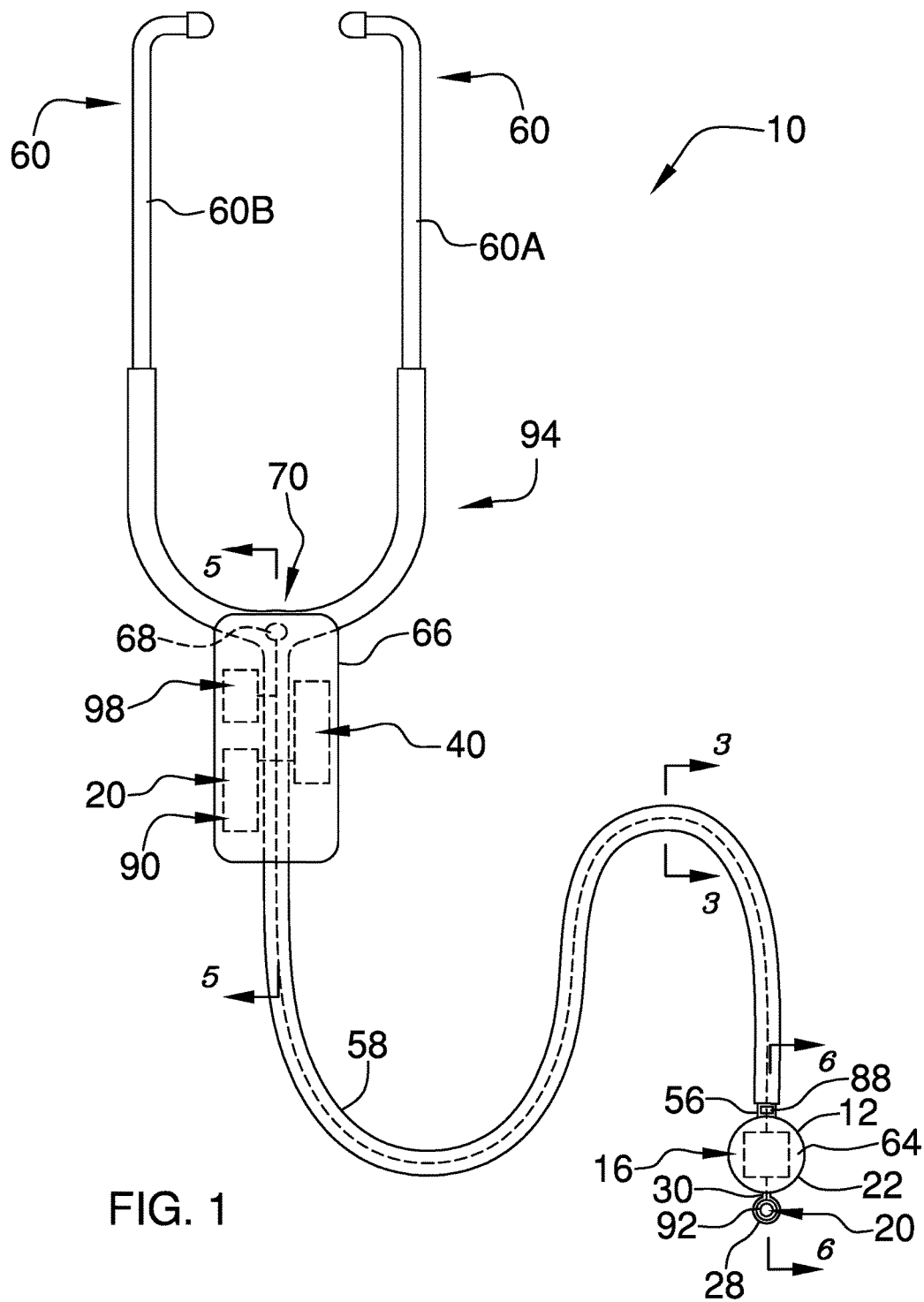
FIG. 1 is a front view of a audible ultrasound physical examination device according to an embodiment of the disclosure.
Figure 2:
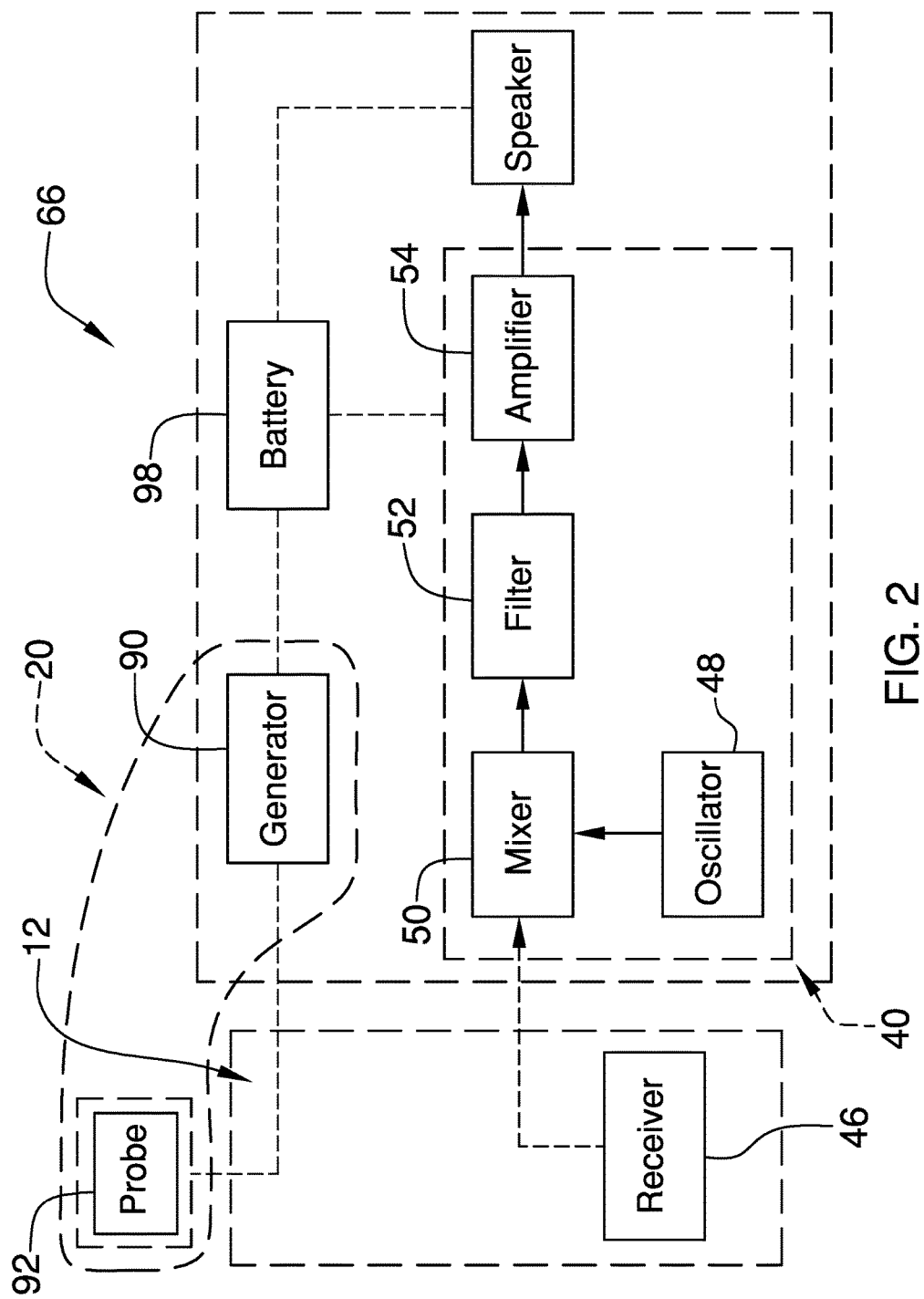
FIG. 2 is a schematic view of an embodiment of the disclosure.
Figure 3:
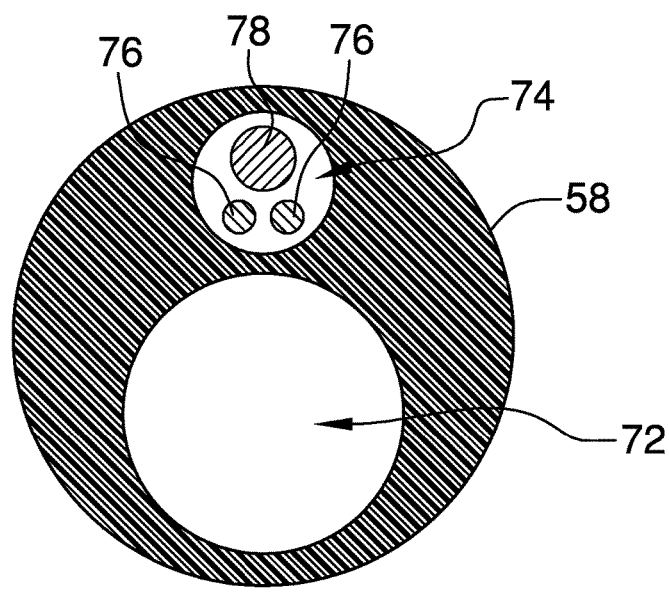
FIG. 3 is a cross-sectional view of an embodiment of the disclosure taken along line 3-3 of FIG. 1.
Figure 4:
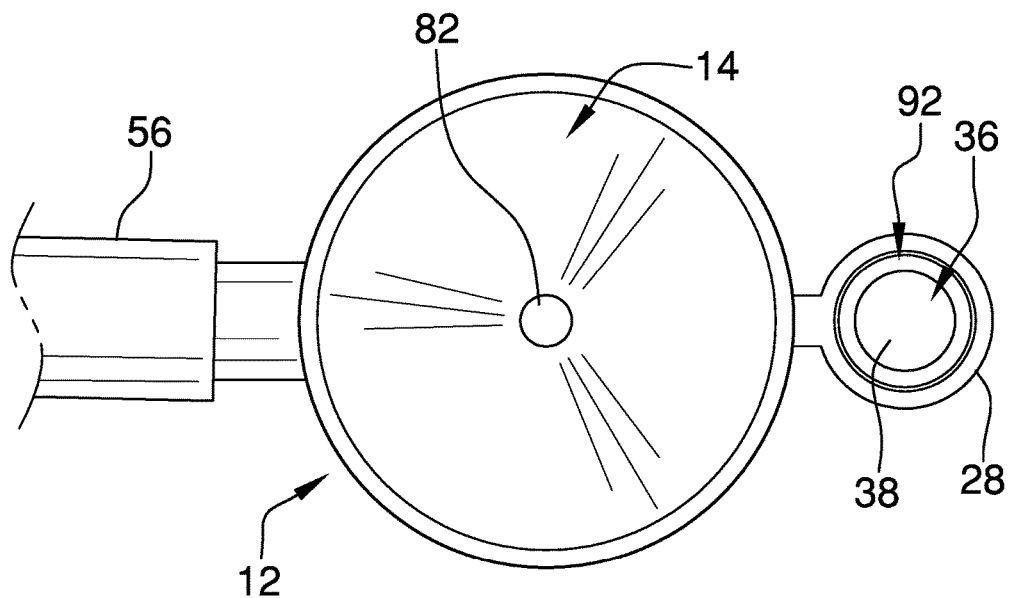
FIG. 4 is a detailed bottom view of an embodiment of the disclosure.
Figure 5:
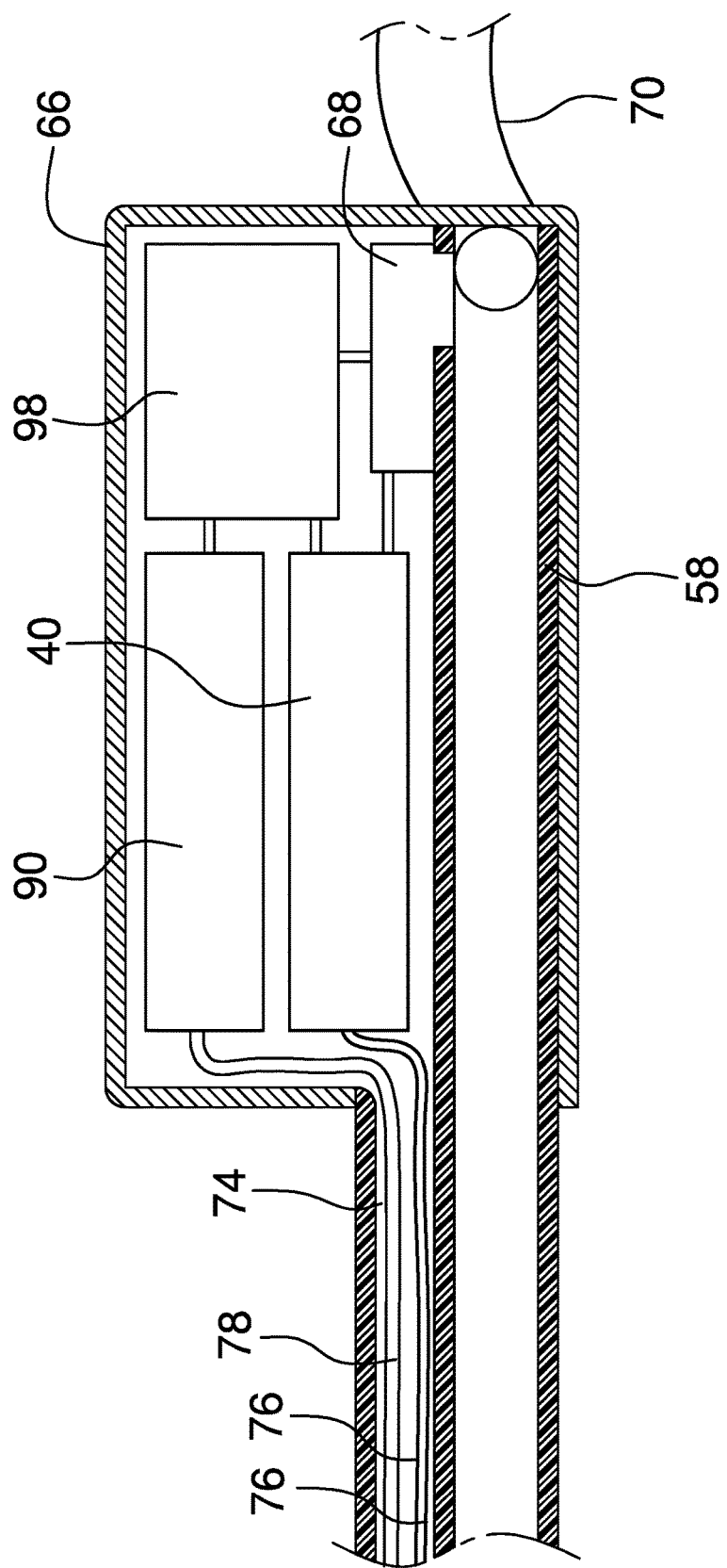
FIG. 5 is a cross-sectional view of an embodiment of the disclosure taken along line 5-5 of FIG. 1.
Figure 6:
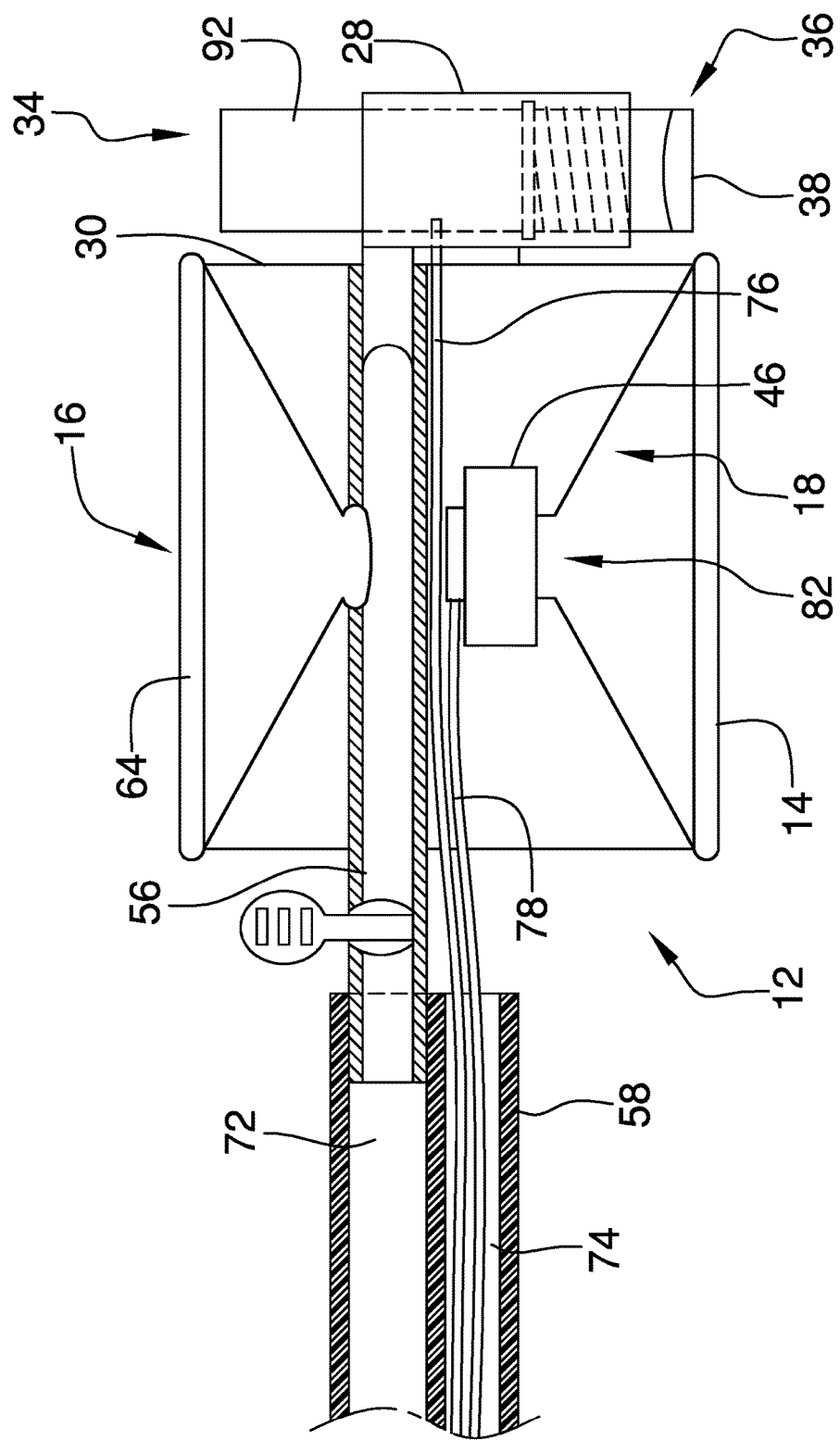
FIG. 6 is a cross-sectional view of an embodiment of the disclosure taken along line 6-6 of FIG. 1.
Figure 7:
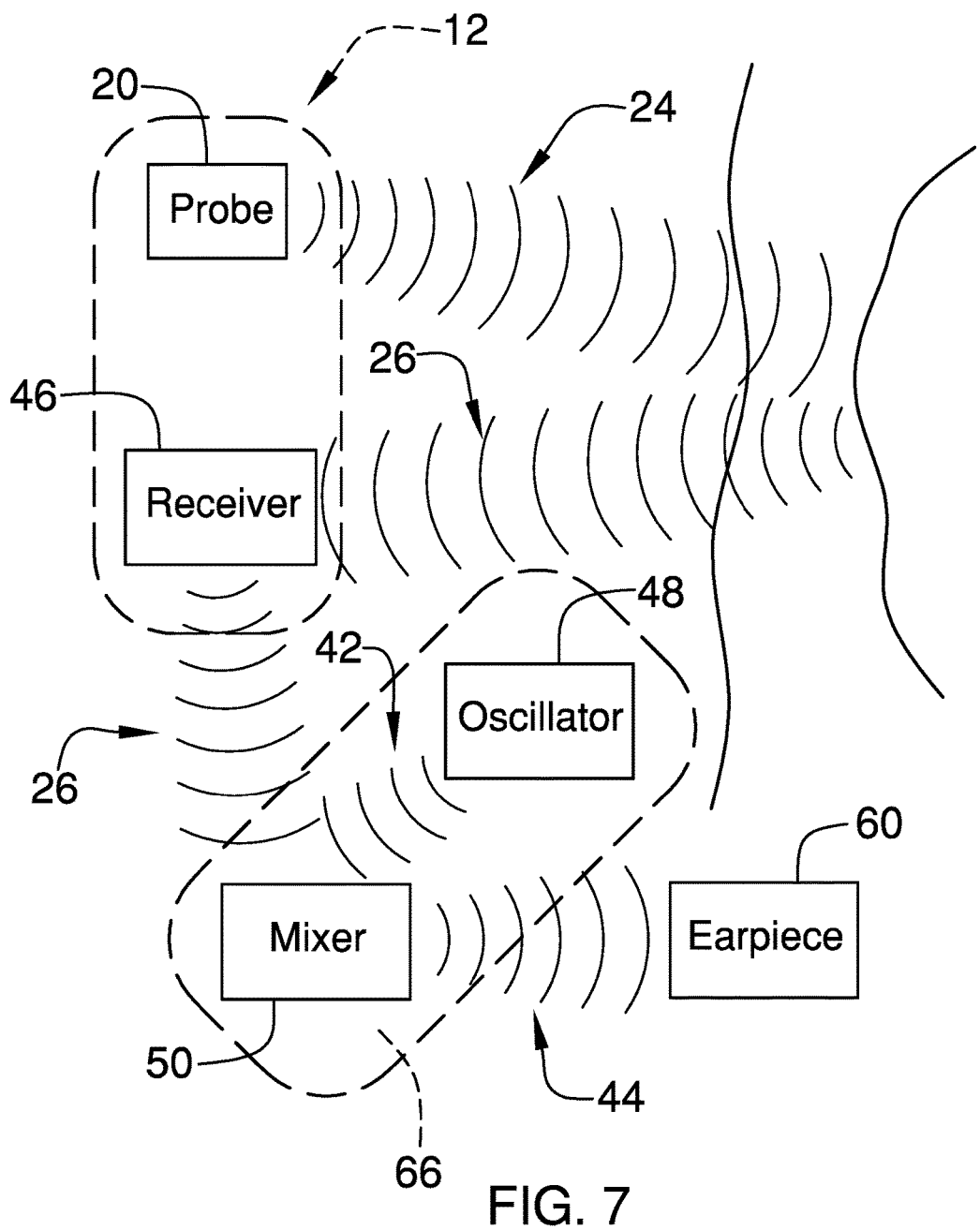
FIG. 7 is a schematic view of an embodiment of the disclosure.

With reference now to the drawings, and in particular to FIGS. 1 through 7 thereof, a new physical examination device embodying the principles and concepts of an embodiment of the disclosure and generally designated by the reference numeral 10 will be described.

As best illustrated in FIGS. 1 through 7, the audible ultrasound physical examination device 10 generally comprises a chestpiece 12 having a first face 14 and a second face 16. The first face 14 defines an open bell 18 of the chestpiece 12. An ultrasound probe 20 is coupled to the chestpiece 12. The ultrasound probe 20 extends from a lateral wall 22 of the chestpiece 12 and is directed generally towards the first face 14 and away from the second face 16. The ultrasound probe 20 is oriented perpendicular to the first face 14. The ultrasound probe 20 projects an initial sound wave 24 in a defined direction away from the second face 16 and towards a patient being examined. Thus, the ultrasound probe 20 is configured for projecting the initial sound wave 24 into a human body such that a reflected wave 26 is produced when the initial sound wave 24 is reflected by matter with the human body. The reflected wave 26 has a changed amplitude dependent on acoustic density of the matter within the human body reflecting the initial sound wave 24 just as in conventional ultrasound machines which use reflected waves to produce a visual image.

A sleeve 28 is coupled to a peripheral surface 30 of the chestpiece 12. The ultrasound probe 20 is mounted within the sleeve 28. The ultrasound probe 20 has a distal end 34 relative to the first face 14. The ultrasound probe 20 is movable within the sleeve 28 to extend a probe end 36 of the ultrasound probe 20 in a direction towards the first face 14 to facilitate use of the ultrasound probe 20 and allow the probe end 36 to contact a patient. The ultrasound probe 20 may be biased to retract away from the first face 14 within the sleeve 28 in a conventional manner using a spring or the like. An acoustic lens 38 is coupled to the ultrasound probe 20 to focus the initial sound wave 24. The ultrasound probe 20 more specifically comprises a primary ultrasound generator 90 positioned in a housing 66 external to the chestpiece 12 and a piezoelectric transducer 92 positioned within the sleeve 28.

A sonic converter 40 is operationally coupled to the chestpiece 12. The sonic converter introduces an interference wave 42 creating destructive interference with the reflected wave 26 to produce a resulting wave 44 within an audible range, meaning audible to a human ear, such that the audible changes in the resulting wave 26 indicating changes in matter type within the human body as the ultrasound probe is moved are audible to the human ear. The interference wave 42 has a higher or lower frequency than the initial sound wave 24, but only higher or lower enough to produce the desired interference producing the audible resulting wave 26. Thus, the difference in frequency would be between 20 Hz and 20 kHz, which is the expanse of the audible range. However, the frequency of the interference wave 42 may be within a sub-range such as being between 0.05 kHz and 1.0 kHz higher or lower than the initial sound wave 24 to produce audible sounds within a desired and comfortable range. The sonic converter 40 is positioned in the chestpiece 12 and the housing 66 external to the chestpiece 12. A piezoelectric receiver 46 is positioned in the chestpiece 12 for receiving the reflected wave 26. The piezoelectric receiver 46 is positioned adjacent to and in communication with a central aperture 82 in the open bell 18 such that the reflected wave 26 is directed to the piezoelectric receiver 46 by the open bell 18. The sonic converter 40 receives the reflected wave 26 from the piezoelectric receiver 46 in the form of a sine wave. The sonic converter 40 includes a local oscillator 48 positioned in the housing 66 which produces the interference wave 42 also in the form of a sine wave. The sonic converter 40 also includes a heterodyne mixer 50 positioned in the housing 66 to mix the interference wave 42 and the reflected wave 26 to produce the resulting wave 44. The sonic converter 40 also includes a filter 52 positioned in the housing 66 which receives the resulting wave 44 from the heterodyne mixer 50 and passes through only the resulting wave 44 to be heard. The sonic converter 40 also includes an amplifier 54 positioned in the housing 66 for amplifying the resulting wave 44 after the resulting wave 44 is passed through the filter 52. A speaker 68 may be coupled to the housing 66 and operationally coupled to the sonic converter 40 for broadcasting the resulting wave 44.

A stem 56 extends from the chestpiece 12. Flexible tubing 58 is coupled to and extends from the stem 56 in a conventional manner as in a conventional stethoscope. An earpiece 60 is coupled to the flexible tubing 58 wherein the earpiece 60 is configured for allowing a person to hear the resulting wave 44 in the audible range and hear changes in the resulting wave 44 as the initial wave 24 is reflected from materials within the body having different densities. The earpiece 60 is coupled to the sonic converter 40 such that the resulting wave 44 in the audible range is audible through the earpiece 60. The earpiece 60 may be biaural and include an upper section 94 of the flexible tubing 58 forming a junction between a left piece 60A and a right piece 60B. A diaphragm 64 defines the second face 16 of the chestpiece 12 wherein the chestpiece 12 and the earpiece 60 are configured for use as a conventional stethoscope when the diaphragm 64 is positioned against the human body. The housing 66 may be provided at a base 70 of the earpiece 60. The flexible tubing 58 has a main conduit 72 and a secondary conduit 74. The main conduit 72 extends between the chestpiece 12 and the earpiece 60 and carries sound from the chestpiece 12 to the earpiece 60 in a conventional manner. The secondary conduit 74 extends between the chestpiece 12 and the housing 66 and houses wiring 76 and cable 78 as needed for operational connection and communication between the ultrasound probe 20, the piezoelectric receiver 46, the sonic converter 40, and a battery 98 positioned within the housing 66. A valve 88 may be coupled to the flexible tubing 58 to selectively close the main conduit 72 when using the ultrasound probe 20. The valve 88 may be positioned proximate to the chestpiece 12.

In use, the device 10 provides an audible contrast between different densities within a human body. Thus, the device 10 may be used as a first indicator of potential health issues such as fluid collection or cancerous masses within the body of a patient. Generally, the ultrasound probe 20 is used in a similar manner to a conventional stethoscope and conventional video producing ultrasound devices. The device 10 is more effective at detecting potential issues than a conventional stethoscope and may be used during initial examination to facilitate early detection of health problems or to more confidently rule out unnecessary more expensive testing such as conventional video producing ultrasound examination or CT scans. Use of the device 10 can also reduce exposure to significant radiation exposure in some testing procedures such as a CT scan.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:
1. An audible ultrasound physical examination device comprising:
   a chestpiece, said chestpiece having a first face and a second face;
   an ultrasound probe coupled to said chestpiece, said ultrasound probe projecting an initial sound wave in a defined direction towards said first face wherein said ultrasound probe is configured for projecting the initial sound wave into a human body such that a reflected wave is produced when said initial sound wave is reflected by matter with the human body whereby said reflected wave has a changed amplitude dependent on acoustic density of the matter within the human body reflecting the initial sound wave;

a sonic converter, said sonic converter being coupled to said chestpiece, said sonic converter introducing an interference wave creating destructive interference with said reflected wave to produce a resulting wave within an audible range such that said audible changes in said resulting wave indicate changes in matter type within the human body as said ultrasound probe is moved; and an earpiece, said earpiece being coupled to said chestpiece such that said resulting wave in said audible range is audible through said earpiece.

2. The device of claim 1, further comprising a diaphragm defining said second face of said chestpiece wherein said chestpiece and earpiece are configured for use as a conventional stethoscope when said diaphragm is positioned against the human body.

3. The device of claim 1, further comprising:
a stem extending from said chestpiece;
flexible tubing coupled to and extending from said stem; and
said earpiece being coupled to said flexible tubing wherein said earpiece is configured for allowing a person to hear said resulting wave in the audible range.

4. The device of claim 1, further comprising:
said first face defining an open bell of said chestpiece; and
said ultrasound probe extending from a lateral wall of said chestpiece, said ultrasound probe being oriented perpendicular to said first face.

5. The device of claim 4, further comprising:
a piezoelectric receiver for receiving said reflected wave, said piezoelectric receiver being positioned in said chestpiece; and
said sonic converter being positioned within a housing external to said chestpiece,
said sonic converter including
a local oscillator, said local oscillator producing said interference wave, and
an heterodyne mixer, said heterodyne mixer mixing said interference wave and said reflected wave.

6. The device of claim 5, wherein said sonic converter further includes a filter, said filter receiving said resulting wave from said heterodyne mixer and passing through only said resulting wave to said earpiece.

7. The device of claim 5, wherein said sonic converter includes an amplifier for amplifying said resulting wave prior to passing said resulting wave through to said earpiece.

8. The device of claim 1, further comprising said interference wave having a higher frequency than said initial sound wave.

9. The device of claim 1, further comprising said interference wave having a lower frequency than said initial sound wave.

10. The device of claim 4, further comprising a sleeve coupled to peripheral surface of said chestpiece, said ultrasound probe being mounted within said sleeve, said ultrasound probe having a distal end relative to said first face, said ultrasound probe being movable within said sleeve to extend a probe end of said ultrasound probe in a direction towards said first face.

11. The device of claim 1, further comprising an acoustic lens coupled to said ultrasound probe.

12. The device of claim 7, further comprising a speaker coupled to said housing, said speaker broadcasting said resulting wave.

13. An audible ultrasound physical examination device comprising:
a chestpiece, said chestpiece having a first face and a second face, said first face defining an open bell of said chestpiece;
an ultrasound probe coupled to said chestpiece, said ultrasound probe extending from a lateral wall of said chestpiece and being directed towards said first face perpendicular to said first face, said ultrasound probe projecting an initial sound wave in a defined direction wherein said ultrasound probe is configured for projecting the initial sound wave into a human body such that a reflected wave is produced when said initial sound wave is reflected by matter with the human body whereby said reflected wave has a changed amplitude dependent on acoustic density of the matter within the human body reflecting the initial sound wave;
a sleeve coupled to peripheral surface of said chestpiece, said ultrasound probe being mounted within said sleeve, said ultrasound probe having a distal end relative to said first face, said ultrasound probe being movable within said sleeve to extend a probe end of said ultrasound probe in a direction towards said first face;
an acoustic lens coupled to said ultrasound probe;
a piezoelectric receiver for receiving said reflected wave, said piezoelectric receiver being positioned in said chestpiece;
a sonic converter, said sonic converter being positioned within a housing external to said chestpiece, said sonic converter introducing an interference wave creating destructive interference with said reflected wave to produce a resulting wave within an audible range such that said audible changes in said resulting wave indicate changes in matter type within the human body as said ultrasound probe is moved, said interference wave having a higher frequency than said initial sound wave, said sonic converter being positioned in said chestpiece, said sonic converter including
a local oscillator, said local oscillator producing said interference wave,
an heterodyne mixer, said heterodyne mixer mixing said interference wave and said reflected wave,
a filter, said filter receiving said resulting wave from said heterodyne mixer and passing through only said resulting wave, and
an amplifier for amplifying said resulting wave after said resulting wave is passed through said filter;
a speaker coupled to said housing, said speaker broadcasting said resulting wave into said flexible tubing wherein said resulting wave is audible through said earpiece;
a stem extending from said chestpiece;
flexible tubing coupled to and extending from said stem,
an earpiece, said earpiece being coupled to said flexible tubing wherein said earpiece is configured for allowing a person to hear said resulting wave in the audible range, said earpiece being coupled to said sonic converter such that said resulting wave in said audible range is audible through said earpiece, said housing being coupled to a base of said earpiece; and
a diaphragm defining said second face of said chestpiece wherein said chestpiece and said earpiece are configured for use as a conventional stethoscope when said diaphragm is positioned against the human body.

* * * * *